United States Patent [19]
Rossetti

[11] Patent Number: 5,201,713
[45] Date of Patent: Apr. 13, 1993

[54] ONE-WAY INTRAVENOUS CATHETER WITH NEEDLE GUARD

[75] Inventor: Alessandro Rossetti, Via del Mare, Italy

[73] Assignee: Critikon, Inc., Tampa, Fla.

[21] Appl. No.: 706,619

[22] Filed: May 29, 1991

[51] Int. Cl.$^5$ .................................. A61M 5/178
[52] U.S. Cl. .............................. 604/165; 604/198
[58] Field of Search ............ 604/263, 198, 164, 162, 604/165, 158, 167, 168, 170

[56] References Cited

U.S. PATENT DOCUMENTS

| | | | |
|---|---|---|---|
| 4,681,567 | 7/1987 | Masters et al. | 604/198 |
| 4,781,692 | 11/1988 | Jagger et al. | 604/164 |
| 4,846,805 | 7/1989 | Sitar | 604/165 |
| 4,850,961 | 7/1989 | Wanderer et al. | 604/53 |
| 4,917,669 | 4/1990 | Bonaldo | 604/164 |
| 5,000,740 | 3/1991 | Ducharme et al. | 604/162 |
| 5,013,304 | 5/1991 | Russell et al. | 604/167 |
| 5,019,049 | 5/1991 | Haining | 604/165 |
| 5,026,351 | 6/1991 | Dizon | 604/164 |
| 5,030,205 | 7/1991 | Holdaway et al. | 604/164 |
| 5,053,014 | 10/1991 | Van Heugten | 604/167 |
| 5,102,394 | 4/1992 | Lasaitis et al. | 604/164 |
| 5,108,376 | 4/1992 | Bonaldo | 604/171 |
| 5,112,311 | 5/1992 | Utterberg et al. | 604/177 |
| 5,120,320 | 6/1992 | Fayngold | 604/177 |

Primary Examiner—John D. Yasko
Assistant Examiner—Mark O. Polutta

[57] ABSTRACT

One-way intravenous catheter assembly provided with a tubular needle guard slidable with respect to the needle housing, so as to completely cover the needle both before and after use, said needle housing comprising a substantially cylindrical central body with a flash chamber and a tapered front portion, to which the catheter needle is attached, and a peripheral finger gripping element, connected to the central body but extending around the tubular needle guard, the connection being provided by a connecting element which is slidable in a longitudinal slot of the tubular needle guard, the catheter assembly being further provided with a catheter tube or cannula mounted around the needle and provided with a hub for engagement with said tapered front portion of the needle housing.

8 Claims, 3 Drawing Sheets

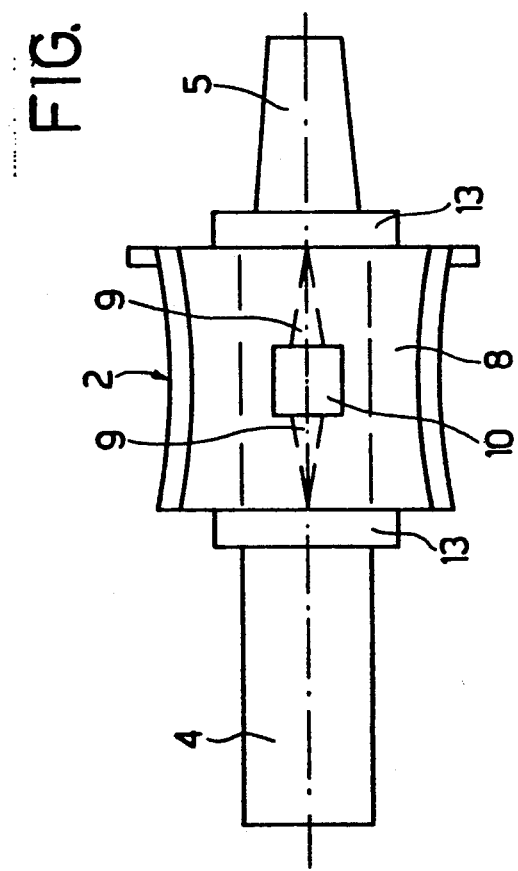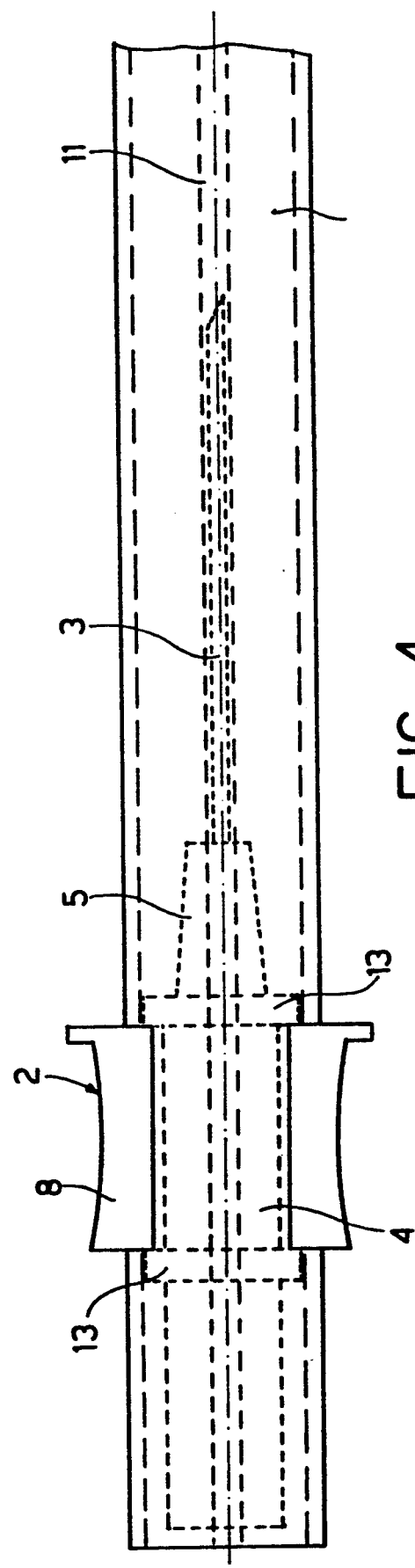

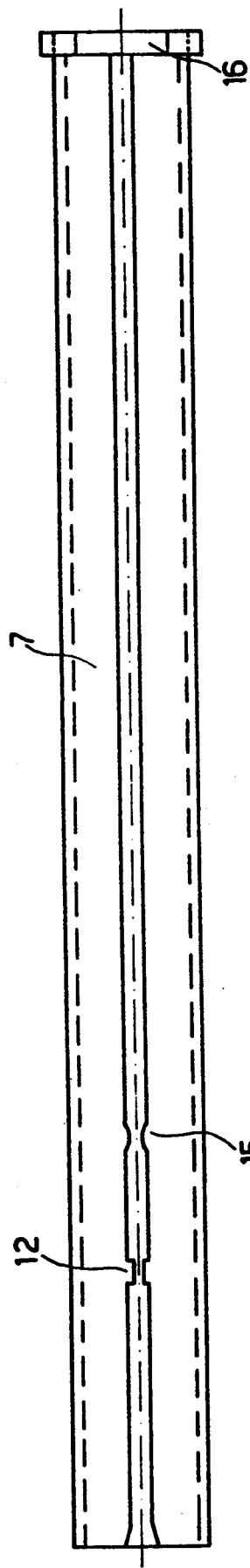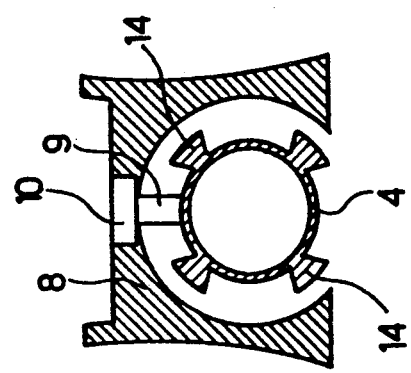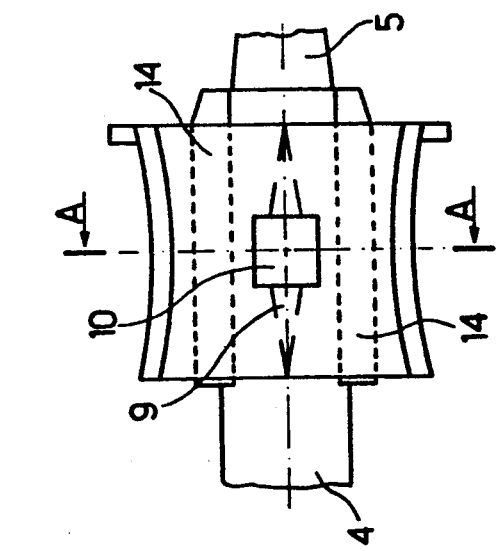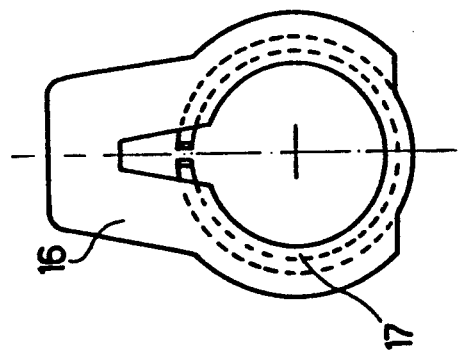

ONE-WAY INTRAVENOUS CATHETER WITH NEEDLE GUARD

FIELD OF THE INVENTION

The present invention relates to a one-way intravenous catheter with needle guard. More specifically, the invention relates to a one-way catheter assembly which allows the retraction of the needle within a protective guard as soon as the catheter tube is placed into a blood vessel, thus protecting the user from accidental needle injury.

BACKGROUND OF THE INVENTION

The conventional one-way intravenous catheter originates from the need of infusing pharmaceutical liquids (flebochlysis) or blood (transfusion) into the venous system, and of drawing blood therefrom (donation).

An intravenous catheter assembly typically comprises a thin teflon tube (cannula), of a size which depends on the required use, attached to a plastic hub, and provided with standard connecting means for connection to the infusion or blood drawing sets. The catheter tube is inserted into the vein of a patient by means of an inner coaxial stainless steel needle, which is withdrawn by retracting it from the catheter tube right after the insertion of the catheter into the patient's vein. The needle is attached to a separate plastic support.

One-way catheters are generally employed in hospitals for administering pharmaceutical solutions directly into the venous system. The only way of the catheter is connected to an infusion set, which is in its turn connected to the container of the liquid to be infused. After that the catheter has been safely placed into the patient's vessel and once the needle is withdrawn from the catheter, the user should dispose of the needle, but very often he connects the infusion set as a first step, and he tapes the catheter on the patient's skin, and just drops the needle nearby, so that he can retreave it and dispose of it later.

The various handlings of the needle, once it has been removed, bring about considerable risk of accidental needle injury, which may have serious consequences if the needle is infected by the patient's blood. This problem is particularly critical in the hospital departments where serious infectious diseases such as hepatitis or AIDS are treated.

In order to reduce the danger coming from used needles, there have been provided plastic sheaths or caps that should be employed to cover the needle right after use, but this operation may easily cause accidental injury right when the sheath is being placed again on the needle.

A device directed to the solution of the above-mentioned problem is disclosed in the U.S. Ser. No. 335,472, filed on Apr. 10, 1989, now U.S. Pat. No. 5,000,740, assigned to a common assignee and incorporated by reference. Such patent comprises the state of the art within the meaning of Article 54 (3) and (4) EPC with respect to the present application.

The one-way catheter disclosed in the above-mentioned patent application comprises a catheter tube or cannula with the relevant hub, a needle located within said cannula and attached to a specially designed plastic housing, a protective needle guard provided with a longitudinal slot which may slide with respect to said housing so as to completely cover the needle, and a removable protective sheath which surrounds the needle and catheter tube prior to use. As initially assembled, the needle guard is completely retracted with respect to the needle housing, and the needle and catheter tube are covered by the above mentioned sheath, which is releasably connected by means of a flange to said needle guard. Prior to use, the sheath is removed and the catheter is inserted into the patient's vessel, as usual. Once the tip of the needle has reached the blood vessel, the user, while holding the device by the needle housing, advances the above mentioned tubular needle guard, thereby disengaging the catheter hub from the needle and causing the retraction of the needle within the needle guard starting from the rear end of the needle.

Thus, the immediate protection of the needle right after use is obtained without requiring the user's hands to pass close to the needle tip, and therefore allowing a quite safe operation. The disclosed device, while affording the required safety, has, however, a rather complex structure and is, accordingly, quite expensive. In particular two additional elements are required, i.e. the protective sheath and the tubular needle guard, whose construction is particularly complicate.

The object of the present invention is therefore to provide a one-way intravenous catheter which allows the same safety and ease of operation as the catheter of the prior art, while being of a simpler construction and involving lower production costs. It is evident that, in order to result in a real contribution to the safety against blood borne diseases, a device of the kind disclosed must be reasonably cheap, so as to be available to a wide market.

SUMMARY OF THE INVENTION

According to the present invention, there is proposed to supply a conventional one-way catheter with a housing element for the needle, substantially in the form of a hollow cylinder, with a peripheral finger grip coaxial to said cylinder and connected to it by means of a longitudinal connecting element, and with one simple tubular needle guard longitudinally cut by a guiding slot, slidable on said longitudinal connecting element of the needle housing, so as to completely surround all the elements of the catheter but the above-mentioned peripheral finger grip. The shape of the said longitudinal connecting element and that of the needle guard slot which cooperates with the former are such as to have an irreversibly locked position with the needle completely retracted within the needle guard.

Since the needle guard has a tubular shape, open at least at the front end, it may slide with respect to the needle housing, and therefore with respect to the whole catheter, between two extreme positions, the first one of complete retraction, with the needle and catheter tube fully uncovered (use position) and the other of complete extension, with the needle (and possibly the catheter tube) completely covered by the needle guard.

The catheter according to the invention does not require the use of a further element such as a sheath, to be placed on the needle in the initial assembly, as the needle is already protected by the tubular needle guard in its fully extended position. Prior to use, the needle guard is pushed backwards, thus uncovering the needle and the catheter tube, and after that the catheter has been placed into the blood vessel, the needle guard is returned to its extended position, thus protecting the needle. At the end of the stroke the locking mechanism of the needle guard locks the needle in the needle housing thereby avoiding any accidental needle injury.

Accordingly, the present invention specifically provides a one-way intravenous catheter with needle guard comprising: a catheter tube or cannula attached to a catheter hub tapered on both its internal and external surfaces; a needle whose outer diameter is sized to fit in said catheter tube, attached to a needle housing substantially in the form of a hollow cylinder, with peripheral finger gripping means in the form of an outer coaxial element, connected to the central body of said needle housing by means of a longitudinal connecting element; a tubular needle guard whose length is greater than the length of the needle and whose inner diameter is sufficient for it to surround all the elements of the catheter but said peripheral finger gripping means, said needle guard being provided with a longitudinal guiding slot cooperating with said longitudinal connecting element for sliding relative to said needle housing, wherein locking means are provided on said slot and connecting element for locking the needle guard in its position totally advanced with respect to the catheter, and wherein the front portion of said needle housing is sized to engage the tapered internal surface of said catheter hub.

Preferably, the central cylindrical portion of said needle housing is provided with two tranversal guiding ribs whose outer diameter is sized to fit the internal surface of the tubular needle guard. As it will be clear with reference to the enclosed drawings, the function of said two transversal ribs is to smoothly guide the sliding of the needle within the needle guard while keeping it perfectly coaxial with the latter. In an alternative embodiment of the invention, there are provided four longitudinal guiding ribs, projecting from said central cylindrical portion of the needle housing and uniformly spaced around it, the height of said ribs being such that said central cylindrical portion fits the internal surface of the tubular needle housing.

According to a preferred embodiment of the invention, said peripheral finger gripping means has a partially interrupted cylindrical internal surface, and a substantially parallelepipedal outer surface with two contoured opposite faces.

The longitudinal connecting element which connects the central body of said needle housing to the peripheral finger gripping means, and which cooperates with said longitudinal slot for guiding said needle guard, is preferably made of two subsequent separate portions both tapered to a greater width towards the central portion of said connecting element, and separated by an aperture in said central portion. In this embodiment the locking means provided on said connecting element are represented by said aperture in the central portion of said connecting element, while the corresponding locking means on the needle guard are represented by two opposed teeth projecting along the guiding slot. Said teeth are such as to irreversibly engage with said aperture in the central portion of the connecting element.

Preferably, said longitudinal slot is provided with a second couple of opposed teeth having a rounded profile and located towards the front end of said needle guard with respect to said two first opposed teeth. As it will be clear with reference to the enclosed drawings, said second couple of teeth provides a non-irreversible pre-lock on which the catheter assembly is positioned before use, in order to prevent accidental sliding of the needle and catheter tube out of the needle guard before use.

In a specific embodiment of the invention, the catheter assembly also comprises a tab projecting upwards from the front end of said tubular needle guard, which may be held by the user when retracting or advancing the needle guard with respect to the needle housing.

The central cylindrical portion of said needle housing is preferably made of a transparent or translucent material, so that said cylindrical central portion may be used as a flash chamber allowing the flow of blood to be apparent as soon as the needle reaches a blood vessel. The flash chamber may be closed by a microporous plug.

The structure of the catheter assembly according to the invention, as well as the relevant use and advantages, will be made clear with reference to some preferred embodiments thereof, which are shown in the enclosed drawings, wherein:

DESCRIPTION OF THE DRAWINGS

FIG. 3 is a front view of the needle housing of the catheter assembly of FIG. 1;

FIG. 4 is a view of the same catheter assembly of FIG. 1 taken from the opposite side and without the catheter tube;

FIG. 5 is a front view of a second embodiment of the needle guard of the catheter assembly according to the invention;

FIG. 6 is lateral view of the needle guard of FIG. 5 taken from the right-hand side and rotated by 90°;

FIG. 7 is a front view of the central portion of a second embodiment of the needle housing according to the invention; and FIG. 8 is a cross sectional view of the needle housing of FIG. 7, taken along the line A—A.

DESCRIPTION OF THE INVENTION

Figure 1:
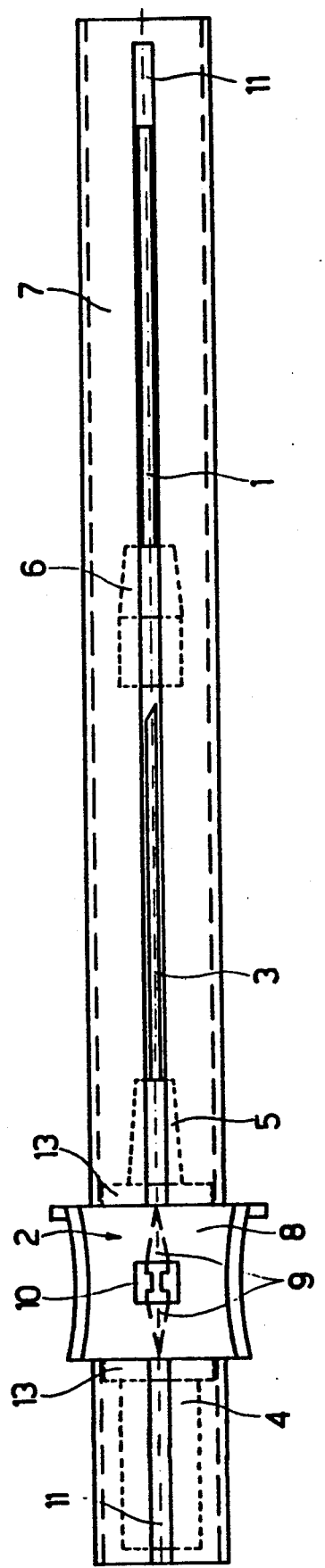
FIG. 1 is a front view of a first embodiment of a one-way catheter assembly with needle guard according to the invention.

FIG. 1 shows a catheter according to the invention with most of its elements and with the catheter tube 1 shown separate for a better understanding.

The needle housing 2 of the needle 3 (shown in detail in FIG. 3) comprises a central body 4 substantially cylindrical, which is attached to the needle 3. The front portion 5 of the needle housing 2 is slightly tapered (male luer ISO) so as to perfectly engage the tapered internal surface of the catheter hub 6 (female luer ISO).

The central body 4 of the needle housing 2 is made of a transparent or translucent material, so as to be used as a flash chamber, and is generally closed by a microporous plug (not shown). Said plug allows the passage of gases while preventing the liquid flow out of the flash chamber and is made of, e.g., non-toxic porous polyethylene. The central body 4 may coaxially slide within a needle guard 7, made of transparent plastic material.

The central body 4 is surrounded by a peripheral finger gripping element 8 coaxial with the catheter, which has an inner interrupted cylindrical surface sized to fit around the tubular needle guard, and an outer surface substantially parallelepipedal, with two contoured opposite sides, so as to be easily gripped by the user with the index finger and the thumb. The gripping element 8 is the only element of the catheter assembly which is not contained within the needle guard 7, but extends around it and almost completely surrounds it. In particular, the gripping element 8 is seen as an integral element in the front views of FIGS. 1 and 3, while in the opposite view of FIG. 4 only two separate sections thereof are visible.

The finger gripping element 8 is connected to the central body 4 of the needle housing 2 by means of a longitudinal connecting element divided into two separate sections 9 shown by broken lines in FIGS. 1 and 3. The cross-section of both sections 9 is tapered towards the central portion of the connecting element, from a smaller to a greater width, and the central portion is interrupted by a square aperture 10.

Figure 2:
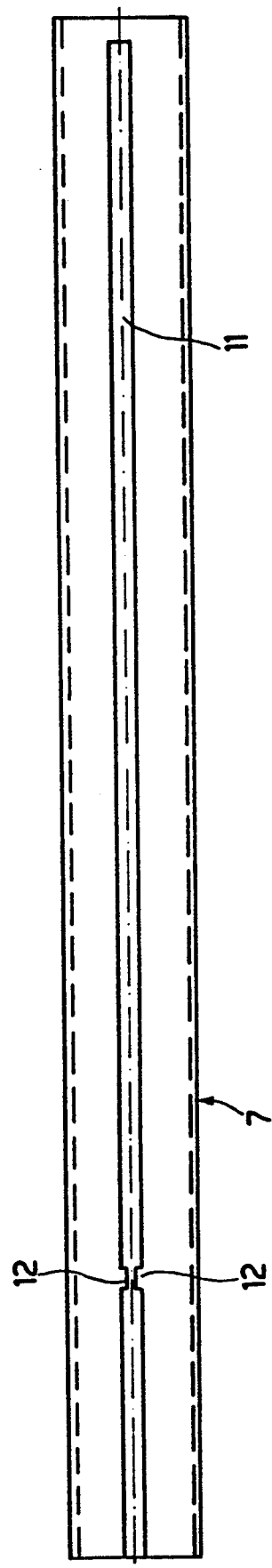
FIG. 2 is a front view of the needle guard of the catheter assembly of FIG. 1.

The needle guard 7, shown in detail in FIG. 2, is supplied with a longitudinal guiding slot 11, which engages with the two sections 9 of the longitudinal connecting element. The slot 11 has two opposed teeth 12 which are part of an irreversible locking mechanism, together with the aperture 10 on the needle housing 2. FIG. 1 shows the needle housing 2 in the locked position, with the teeth 12 engaged in the aperture 10. The tapered cross-section of the sections 9 of the connecting element is designed to guide the two teeth 12 apart from each other while the needle housing 2 slides with respect to the needle guard 7, until the locking position is reached.

When advancing the needle 3 and catheter 6 and 1 prior to use, the longitudinal slot 11 cooperates with the two sections 9 of the connecting element in guiding the needle housing 2 out of the needle guard 7. After that the catheter tube 1 has been placed into the patient's vein the same guiding system helps the retraction of the needle 3 within the needle guard 7. When the needle housing 2 is pushed towards a position fully retracted with respect to the needle guard 7, the two teeth 12 on the slot 11 cooperate with the sections 9 of the connecting element and irreversibly lock the catheter assembly in the position shown in FIG. 1. The latter position is reached after use, when the catheter assembly, deprived of the catheter tube 1 and hub 6, is going to be disposed of.

In order to obtain a perfect coaxiality of the needle housing 2 with the needle guard 7, two transversal guiding ribs 13 are provided around the central body 4 of the needle housing 2. The outer diameter of the guiding ribs 13 is such that they perfectly fit within the tubular needle guard 7.

A different embodiment of the needle housing 2 is shown in FIGS. 7 and 8, where corresponding elements are shown by the same numerals as in the previous figures. The four longitudinal guiding ribs 14 have the same function as the two transversal guiding ribs 13 of FIGS. 1, 3 and 4.

A second embodiment of the needle guard of the invention is shown in FIGS. 5 and 6, where corresponding elements are shown by the same numerals as in the previous figures. In this embodiment, a pre-lock formed by the teeth 15 has been added, in order to provide a stable position in which the catheter assembly can be stored before use, thereby avoiding that the needle 3 accidentally slides out of the housing 7 e.g. during transport. Since the pre-lock position must not be irreversible, the two teeth 15 have a rounded profile.

A further feature of the embodiment shown in FIGS. 5 and 6 is the tab 16, projecting upwards from the front end of the needle guard 7. The tab 16 may be gripped while making the needle guard 7 slide with respect to the needle housing 2. As shown in FIG. 6, the inner diameter of the collar 17 of the tab 16 is slightly smaller than inner diameter of the needle guard 7. When the catheter hub 6, mounted on the needle 3, is pushed forward for use, it is made to pass the narrowed section of the collar 17 by means of a slight pressure. As a result, the catheter hub 6 and tube 1 are prevented from being retracted together with the needle 3 after that the catheter tube has reached the blood vessel, as the catheter hub 6 abuts on the collar 17.

It is evident from the foregoing that the catheter assembly according to the invention affords the highest safety against accidental needle injury, as it prevents the needle tip from coming into contact with the user's hands either before use or after. In particular, no additional sheath is to be removed before use, and the used needle is retracted within the needle guard as it is extracted from the patient's blood vessel.

Furthermore, the construction of the catheter assembly according to the invention is particularly simple, and the relevant production costs may be expected to be reasonably low.

I claim:

1. One way intravenous catheter with needle guard comprising:
    a hollow catheter attached to a hollow catheter hub, said catheter hub having tapered inner and outer surfaces and a proximal and distal end so that the proximal end of said hub is larger in diameter than the distal end of said hub attached to said catheter;
    a hollow cylindrical needle having a diametral size capable of fitting within said catheter, and having a proximal end and a sharpened distal tip;
    a needle housing at the proximal end of said needle, said needle attached to said needle housing, said needle housing having a generally cylindrical shape and further containing a pair of peripheral finger gripping means, said finger gripping means connected to said generally cylindrical shaped housing by a longitudinal connecting element containing a central portion;
    a hollow tubular needle guard with an internal and external surface and a proximal end and distal end, and having a length greater than the needle and needle housing combination, said needle guard having a diameter capable of surrounding both said cylindrical shaped portion of said needle housing and said catheter attached to said needle, and said needle guard provided with a longitudinal slot extending for the length of said needle guard with said slot terminating at one end of said needle guard, said slot allowing passage of said longitudinal connecting element therein, and said needle guard configured to allow said finger gripping means to slide peripherally around said needle guard;
    said needle guard containing locking means and said connecting element containing opposite locking means capable of interengaging said needle guard locking means; and
    said needle housing containing a plurality of longitudinally extending guiding ribs, said guiding ribs capable of engaging the internal surface of said needle guard in sliding relationship thereon along the entire length of said needle guard.

2. The catheter of claim 1 wherein there are two said guiding ribs.

3. The catheter of claim 1 wherein there are four said guiding ribs.

4. Catheter according to claim 1 wherein said peripheral finger gripping means has a generally cylindrical internal surface which is placed in sliding relation with said needle guard, and a substantially parallelepipedal outer surface with two contoured opposite faces.

5. Catheter according to claim 1 wherein said longitudinal connecting element which connects the central body of said needle housing to the peripheral finger gripping means, and which cooperates with said longitudinal slot for guiding said needle guard, is made of two subsequent separate portions both tapered to a greater width towards the central portion of said connecting element, and separated by an aperture in said central portion, and wherein said locking means provided on said connecting element consists of an aperture contained within said longitudinal connecting element, while the corresponding locking means on said needle guard consists of two opposed teeth projecting from said guiding slot capable of engaging said aperture.

6. Catheter according to claim 1 wherein said longitudinal slot is provided with a second couple of opposed teeth having a rounded profile and located towards the distal end of said needle guard with respect to said two first opposed teeth.

7. Catheter according to claim 1 wherein said central cylindrical portion of said needle housing is made of a transparent or translucent material.

8. Catheter according to claim 1 further comprising a tab projecting upwards from the front end of said needle guard.

* * * * *